United States Patent [19]

Hackett et al.

[11] Patent Number: 5,225,541
[45] Date of Patent: * Jul. 6, 1993

[54] COMPOSITION CONTAINING CEA/NCA-SPECIFIC MONOCLONAL ANTIBODY XMMBR-B14 CONJUGATED TO A DETECTABLE MOIETY AND A KIT CONTAINING THE ANTIBODY

[75] Inventors: Adeline J. Hackett; Shahnaz H. Dairkee, both of Orinda, Calif.

[73] Assignee: Peralta Cancer Research Institute, San Leandro, Calif.

[*] Notice: The portion of the term of this patent subsequent to Aug. 1, 2006 has been disclaimed.

[21] Appl. No.: 388,543

[22] Filed: Aug. 1, 1989

Related U.S. Application Data

[60] Division of Ser. No. 158,086, Feb. 16, 1988, Pat. No. 4,853,464, which is a continuation of Ser. No. 21,922, Mar. 5, 1987, abandoned.

[51] Int. Cl.⁵ .............. C07K 15/28; C12N 5/20; A61K 43/00; G01N 33/53
[52] U.S. Cl. .............. 530/391.3; 530/387.3; 530/388.85; 424/1.1; 424/85.8; 435/240.27; 435/172.2; 435/70.21; 435/7.23; 435/188
[58] Field of Search ............. 424/1.1, 85.8, 85.91, 424/86, 87; 514/2, 8, 21; 530/387, 388, 389, 390, 391, 392, 393, 403, 395, 806, 808, 828, 391.3, 387.7, 388.85; 435/240.2, 240.27, 70.21, 172.2, 7.23, 188

[56] References Cited

U.S. PATENT DOCUMENTS 4,145,336 3/1979 Edgington et al. ............. 530/395
4,349,528 9/1982 Koprowski et al. ............ 435/7.23
4,590,071 5/1986 Scannon et al. .............. 424/85.91
4,708,862 11/1987 Baldwin ....................... 424/1.1

FOREIGN PATENT DOCUMENTS 0088695 9/1983 European Pat. Off. .

OTHER PUBLICATIONS

Hird et al. in Carney et al. Eds. "Genes and Cancer", John Wiley & Sons, pp. 183–189, 1990.
Waldmann Science 252:1657–1662 1991.
Spalding Biotechnology 9:901–904 1991.
Price (1988) Br. J. Cancer 57:165–169.
Price et al. (1984) IRCS Med. Sci. 12:1000–1001.
Mach et al. (1980) New Engl. J. Med. 303:5–10.
Goldenberg et al. (1978) New Engl. J. Med. 298:1384–1388.
Thorpe et al. (1982) Immun. Rev. 62:136–138.
Kohler and Milstein (1975) Nature 256:495–497.
Price et al. IRCS Med. Sci. 13:366–367 (1985).
Haspel et al. (1985) "Monoclonal Antibodies and Cancer Therapy" pp. 505–522 Alan R. Liss, Inc. (eds).
Griffin et al. (1982) JNCI 69:799–804.

Primary Examiner—David L. Lacey
Assistant Examiner—Paula Hutzell
Attorney, Agent, or Firm—Townsend and Townsend Khourie and Crew

[57] ABSTRACT

The present invention provides a composition consisting of a monoclonal antibody that defines an epitope found on an antigen antigen/normal cross-reacting antigen produced by hybridoma XMMBR-B14 (HB 9308) conjugated to a detectable moiety, and a kit containing the antibody. Hybridoma XMMBR-B14 was deposited with the ATCC on Jan. 14, 1987 and given the ATCC Accession No. HB 9308.

2 Claims, No Drawings

COMPOSITION CONTAINING CEA/NCA-SPECIFIC MONOCLONAL ANTIBODY XMMBR-B14 CONJUGATED TO A DETECTABLE MOIETY AND A KIT CONTAINING THE ANTIBODY

This is a divisional application of Ser. No. 07/158,086, filed on Feb. 16, 1988, now U.S. Pat. No. 4,853,464, which was a file wrapper continuation of application Ser. No. 07/021,922, filed on Mar. 5, 1987, abandoned.

BACKGROUND OF THE INVENTION

1. Field of the Invention

The present invention relates generally to hybridoma cell lines and, more particularly, to a hybridoma cell line that secretes a monoclonal antibody defining an epitope found on an antigen of the classification termed CEA/NCA (carcinoembryonic antigen/normal cross-reacting antigen).

Monoclonal antibodies (MoAbs) binding epitopes on tumor associated antigens are potent weapons in the ongoing fight against cancer. MoAbs belong to a broad classification of immunologically important compositions of matter called immunoglobulins, which include whole antibodies and active (binding) fragments thereof. For the most part, MoAbs are secreted by hybridoma cells which are produced by combining normal antibody-forming cells with immortal immune cells, such as myeloma cells.

Carcinoembryonic antigen is a cell surface antigen found on a variety of neoplasms, including forms of ovarian, colorectal and breast cancer. It is called CEA because it is present in high concentrations in embryonic cells but is repressed in adult cells. It occurs in low concentrations in normal tissue including breast and colorectal and in high concentrations in neoplastic cells probably because it is derepressed.

CEA is a large glycoprotein which has two antigenically distinct regions. The first is NCA (Normal Colon or Cross-reacting Antigen) which is shared in relatively high concentrations with a different protein present on a wide range of normal tissues (ex. colon, lung, breast). The second region (CEA) is antigenically distinct; therefore antibodies directed against this molecule can be differentiated into: 1) CEA only — little cross-reacting with NCA; 2) CEA/NCA — cross reacts with a wide range of normal tissues including granulocytes.

MoAbs find particular utility as the targeting moiety of immunotoxin and immunoimaging conjugates employed in the diagnosis and treatment of neoplasia. There is therefore an ongoing need for the development of novel hybridoma cell lines that secrete MoAbs defining epitopes on tumor associated antigens such as CEA/NCA.

DESCRIPTION OF THE RELEVANT LITERATURE

Köhler and Milstein, *Nature* (1975)256:495-97, describe continuous cultures of fused cells secreting antibody of predefined specificity.

SUMMARY OF THE INVENTION

The present invention provides a novel hybridoma cell line secreting monoclonal antibodies (MoAbs) that define an epitope found on an antigen of the classification termed CEA/NCA (carcinoembryonic antigen/-normal cross-reacting antigen). The MoAbs of the invention find particular utility as the targeting moiety of immunotoxin and immunoimaging conjugates.

DETAILED DESCRIPTION OF THE PREFERRED EMBODIMENTS

According to the present invention, novel monospecific immunoglobulin compositions are secreted by murine hybridoma cells formed by the fusion of murine myeloma cells and murine spleen cells following immunization with CEA/NCA antigen. As will be appreciated by those skilled in the art, any methodology resulting in the production of immunoglobulins that bind epitopes on CEA/NCA may be employed according to the invention, including, but not limited to, recombinant DNA technology, synthetic protein chemistry and human hybridoma technology.

The immunoglobulins of the present invention are employed for the most part as targeting agents for directing cytotoxic and diagnostic agents to cancer cells within a cancer cell host. According to the present invention, immunoglobulins which define an epitope on an antigen of the classification termed CEA/NCA (carcinoembryonic antigen/ normal cross-reacting antigen) are provided. This antigen is present on a variety of cancers including, but not limited to, colorectal carcinoma, ovarian carcinoma and breast carcinoma.

The immunoglobulins may, but need not, be chemically modified to produce a derivative or conjugate. Various chemical moieties may be coupled to the immunoglobulin to produce conjugates. Such moieties may be, but are not limited to, enzymes, chromaphores, nuclides, cofactors, therapeutic agents (e.g., cytotoxins, nuclides, etc.), and the like. Immunoglobulins or fragments thereof that are linked to such moieties are termed "conjugates." One conjugate of particular interest is comprised of an antibody or fragment thereof linked to a cytotoxin such as, but not limited to, the A-chain (or fragment of A-chain) of ricin, diphtheria or similar toxins. See U.S. Pat. No. 4,590,071 and references cited therein which is incorporated herein by reference.

Chemical modification of the immunoglobulin may involve one or more steps. For example, it may be desirable to provide the immunoglobulin with one or more linking groups prior to final assembly of a conjugate. Examples of linking groups include disulfide addition to amino groups utilizing a heterobifunctional linker such as N-succinimidyl 3-(2-pyridyldithio)propionate (SPDP), or the like, or include carboxyl groupsulfhydryl addition utilizing carbodiimide and the linker mercaptoethylamine (MEA) or the like. Since standard chemical procedures are well known in the art, almost any means of chemically modifying proteins can be used to derivatize immunoglobulins.

Covalent attachment of moieties to the immunoglobulin molecule may be accomplished by reaction of amino acid residues of the amino groups of lysine, the free carboxylic acid groups of glutamic and aspartic acid, the sulfhydryl groups of cysteine or by sulfhydryl group linkers and the various side chains of the aromatic amino acids, as described in EPO Publication No. 0088695, the disclosures of which are hereby incorporated by reference.

The conjugates or unconjugated immunoglobulins may be administered to a cancer cell host either singly or in a cocktail containing two or more conjugate or immunoglobulin formulations, other chemotherapeutic agents, compositions, or the like. Cocktails are particularly important in the treatment of heterogeneous tumor cell populations wherein targeting of multiple antigens is critical.

The conjugates or unconjugated immunoglobulins may be administered to a cancer cell host by any convenient method. Pharmaceutical compositions employing the subject compositions may be administered parenterally, i.e., intravenously, intraparitoneally, or the like. Thus, this invention provides compositions for parenteral administration which comprise a solution of pyrogen free, cytotoxic conjugates or unconjugated immunoglobulin, or a cocktail thereof, dissolved in an acceptable carrier, preferably an aqueous carrier. A variety of aqueous carriers can be used, e.g., water, buffered water, 0.4% saline, 0.3% glycine, or the like. These solutions are sterile and generally free of particulate matter. These compositions may be sterilized by conventional, well-known filtration sterilization techniques. The compositions may contain pharmaceutically acceptable auxiliary substances as required to approximate physiological conditions such as pH adjusting and buffering agents, toxicity adjusting agents, or the like, for example, sodium acetate, sodium chloride, potassium chloride, potassium chloride, calcium chloride, sodium lactate, etc.

The compositions of the present invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss and that use levels may have to be adjusted to compensate.

Single or multiple administrations of the compositions can be carried out with dose levels and pattern being selected by the treating physician. In any event, the pharmaceutical formulation should provide a quantity of composition(s) of this invention sufficient to effectively treat or detect cancer cells. The dose of composition or cocktail will vary widely, generally from about 0.01 mg/kg/day to 20.0 mg/kg/day, usually about 0.05 mg/kg/day to 10.0 mg/kg/day, and, more particularly, 0.05 mg/kg/day to 5.0 mg/kg/day.

Kits may also be supplied for use with the subject compositions or cocktails. Thus, the subject compositions may be provided, usually in lyophilized form, either alone or in conjunction with additional chemotherapeutic agents for cancer therapy or detection. These kits may include buffers, such as phosphate buffered saline, other inert ingredients, or the like. The kits may also include specific instructions including suggested protocols for the administration of the subject compositions to a cancer cell host.

The following examples are offered by way of illustration and not limitation.

EXPERIMENTAL

A. Production of XMMBR-B14 Hybridomas

Balb/c mice were immunized with 521AM whole cells derived from ascites breast metastasis. The immunization schedule consisted of 6 intraperitoneal injections of $10^6$ cells at weekly intervals. A final intravenous boost of $3 \times 10^5$ cells was given 3 days prior to fusion.

Three days after the last antigen boost, spleen cells from an immunized mouse were aseptically removed. A single cell suspension was obtained using an 80 mesh wire screen grid #1985-00080 (Bellco). Cells were washed with Iscoves Complete Medium (Grand Island. N.Y., N.Y.) and counted. Sp2/0-Ag14 cells (A.T.C.C. Accession No. CRL 1581), a hypoxanthine-aminopterin-thymidine (HAT) sensitive murine myeloma cell line, were washed 3 times and counted. Using polyethylene glycol (PEG 4000 Merck) 30% v/v, 10% DMSO and 60% Iscoves, the two cell types were fused at a ratio of 2 spleen cells per myeloma cell. The fusion products were plated into 96-well culture plates at a concentration of $10^5$ myeloma cells per well. Cells were cultured in Iscoves with 20% fetal bovine serum and $\beta$ mercaptoethanol with HAT medium (hypoxanthine 136 mg/100 ml, aminopterin 0.018 mg/100 ml, thymidine 136 mg/100 ml).

Within two weeks post fusion, cultures of hybridoma cells were tested for antibody binding to 521 AM tumor cell membranes by dotting onto nitrocellulose membranes at 200 ng using a Vector Labs ABC kit to test for reactivity. Wells that gave a a blue dot were then screened against fibroblast membrane extracts from the same patient. Cultures that were positive were cloned using limiting dilution, plating 1-3 cells/well into 96 well culture plates. Wells containing only one colony were identified by microscopic examination, then tested for reactivity. The clone designated XMMBR-B14 was found to stably secrete immunoglobulin which was determined to be of the IgG1 subclass. Hybridoma XMMBR-B14 is presently on deposit with the American Type Culture Collection (A.T.C.C.), 12301 Parklawn Dr., Rockville, Md. 20852, USA. The deposit was made on Jan. 14, 1987, and given A.T.C.C. Accession No. HB 9308.

Balb/c mice (Bantin & Kingman, U.K.). 6-10 weeks old, were used to culture the hybridoma peritoneally. Approximately $10^7$ hybridoma cells were injected into mice that had been pretreated 3 weeks earlier with 0.5 mls of pristane (Aldridge, Gillingham, Dorset, U.K.) injected intraperitoneally (i.p.). The resultant ascites fluid, collected 3 weeks after injection of the hybridomas, contained on average 5 mg/ml of the antibody as determined by measuring immunoglobulin level according to the method of Price and Baldwin *ICRS Med. Sci.* (1984) 12:1000-01, which is incorporated by reference.

The antibody in ascites fluid was purified by affinity chromatography using a Sepharose - Protein A column using methods well known by those skilled in the art.

The hybridoma was grown and cloned in vitro in Iscoves Medium with 20% fetal bovine serum and $\beta$ mercaptoethanol in plastic 300 ml bottles. Cell concentration was $10^5$ cells/ml medium over a culturing period of 4-5 days, with a MoAb concentration of 4 $\mu$g/ml medium, and a doubling time of 12 hours.

B. In Vitro XMMBR-B14 Binding to Cells Measured by Flow Cytometry

The binding of XMMBR-B14 to cell lines and primary carcinoma-derived cells was determined by flow cytometry employing methods well known by those skilled in the art and described above. The tests (Table I) showed that XMMBR-B14 detects an antigen expressed on breast and colon carcinoma cell lines. Further studies using purified protein preparations have established that the epitope defined by XMMBR-B14 is found on an antigen of the classification termed CEA/NCA (carcinoembryonic antigen/normal cross-reacting antigen). This is the portion of the CEA molecule that also cross-reacts with exposed normal cross-reacting antigen. It also reacts with cells derived from two primary colon carcinomas. Normal mouse immunoglobulin (NMIg) or normal mouse serum (NMS) were used as controls.

TABLE I

Binding to Various Cells by Flow Cytometry

| Target Cell. | Reagent | Fluorescence Units/cell | Reaction |
|---|---|---|---|
| 1. Cell Lines | | | |
| Colon Carcinoma C170 | NM Ig | 19.3 | — |
| (Low CEA) | B14B8 | 60.4 | ± |
| Colon Carcinoma LS174T | NM Ig | 22.2 | — |
| (Line 1) | B14B8 | 2641.7 | 4+ |
| Colon Carcinoma LS174T | NM Ig | 18.6 | — |
| (Line 2) | B14B8 | 1665.6 | 3+ |
| Breast Carcinoma BT474-3 | NM Ig | 17.3 | — |
| | B14B8 | 316.4 | 1-2+ |
| 2. Primary Colon Carcinoma - Derived Cells | | | |
| C212 | NMS | 31.4 | — |
| | B14B8 | 607.5 | 3+ |
| C213 | NMS | 33.8 | — |
| | B14B8 | 836.8 | 4+ |

C. XMMBR-B14 Reactivity With Colon Carcinoma and Normal Colonic Mucosa Measured by Enzyme Immunoassay (EIA)

XMMBR-B14 was tested for reactivity with primary colon carcinoma membrane and normal colonic mucosa using standard EIA methods well known by those skilled in the art. The test, summarized in Table II, shows that XMMBR-B14 reacts with colon carcinoma membrane.

TABLE II

Binding to Colon Membrane by EIA

| | ELISA Units (OD) | | |
|---|---|---|---|
| Reagent | Normal Colon membrane (NP$_1$) | Colon Carcinoma Membrane (TP$_1$) | | CEA Prep. (B4058) |
| | | (TP$_1$) | (T186) | (B4058) |
| XMMBR-B14 | 0.130 | 0.581 | 0.758 | 0.665 |

TP$_1$ - membrane preparation from pooled primary colon carcinoma.
NP$_1$ - membrane preparation from pooled normal colonic mucosa (from colon cancer patient).
T186 - membrane preparation - primary colon carcinoma T186.
CEA(B4058) - CEA preparation - semi-purified from liver metastasis of colon carcinoma

D. XMMBR-B14 Binding to CEA and NCA

The Reactivity of XMMBR-B14 with CEA and NCA preparations was determined by a solid phase radioimmunoassay. Briefly, antigen preparations were coated into wells of microtest plates. Monoclonal antibody was then added, incubated 1 to 2 hours and wells washed. $^{125}$I-labelled (F(ab) 2 fragments of rabbit anti-mouse IgG were then added to detect bound murine MoAb.

In the first test MoAb binding to semi-purified CEA (Rogers) and NCA (B3991) was compared (Table III). XMMBR-B14 bound to both NCA and CEA (NCA:-CEA ratio 1.2:7).

TABLE III

Binding of XMMBR-B14 to CEA and NCA

| | Mean CPM ± SD (— Background) Bound to: | |
|---|---|---|
| Antibody | CEA (Rogers) | NCA (B3991) |
| Anti-CEA | 1427 ± 222 | 443 ± 48 |
| XMMBR-B14 | 2558 ± 114 | 955 ± 140 |

The present invention provides efficacious, novel compounds and methods useful in the diagnosis and treatment of various cancers. The subject immunoglobulins may be administered to a host in unconjugated or conjugated form either alone or in combination with other compositions including, but not limited to, immunoglobulins, conjugates, chemotherapeutic compositions, antibiotics, immunosuppressive agents, other drugs, excipients, or the like.

Although the present invention has been described in some detail by way of illustration and example for purposes of clarity of understanding, it will be obvious that certain changes and modifications may be practiced within the scope of the appended claims.

What is claimed is:

1. A composition comprising a monoclonal antibody having all of the identifying characteristics of that produced by hybridoma cell line XMMBR-B14 having A.T.C.C. Accession No. HB9308 conjugated to a detectable moiety selected from the group consisting of enzymes, chromophores and nuclides.

2. A kit comprising a monoclonal antibody having all of the identifying characteristics of that produced by hybridoma cell line XMMBR-B14 having A.T.C.C. Accession No. HB9308 and instructions setting forth protocols for the use of such antibody.

* * * * *